United States Patent [19]

Balgorod

[11] Patent Number: 5,102,409
[45] Date of Patent: Apr. 7, 1992

[54] METHOD AND APPARATUS FOR MODIFICATION OF CORNEAL REFRACTIVE PROPERTIES

[76] Inventor: Barry M. Balgorod, 200 E. 72nd St., Suite 16H, New York, N.Y. 10021

[21] Appl. No.: 684,141

[22] Filed: Apr. 11, 1991

Related U.S. Application Data

[63] Continuation of Ser. No. 184,822, Apr. 22, 1988, abandoned.

[51] Int. Cl.$^5$ ............................................. U61N 5/06
[52] U.S. Cl. ....................................... 606/5; 606/13; 606/18; 128/395; 279/121.6; 279/121.680; 279/121.690; 279/121.750
[58] Field of Search .................... 606/5, 13, 17, 18; 128/345, 347, 398; 219/121.6, 121.66–121.69, 121.73–121.75, 121.78–121.81

[56] References Cited

U.S. PATENT DOCUMENTS

| | | | |
|---|---|---|---|
| 3,621,181 | 11/1971 | Young | 219/121 LU |
| 3,769,963 | 11/1973 | Goldman et al. | 128/303.1 |
| 3,865,114 | 2/1975 | Sharon | 128/303.1 |
| 3,965,327 | 6/1976 | Ehlscheid | 219/121 LP |
| 3,982,541 | 9/1976 | L'Esperance | 128/303.1 |
| 4,044,936 | 8/1977 | Obersby | 219/121 LU |
| 4,135,902 | 1/1979 | Oehrle | 219/121.66 |
| 4,164,222 | 8/1979 | Prokhorov et al. | 128/303.1 |
| 4,170,726 | 10/1979 | Okuda | 219/121 LM |
| 4,173,980 | 11/1979 | Curtin | 128/303.1 |
| 4,215,263 | 7/1980 | Grey et al. | 219/121.74 |
| 4,215,694 | 8/1980 | Isakov et al. | 128/303.1 |
| 4,266,548 | 5/1981 | Davi | 128/303.1 |
| 4,309,998 | 1/1982 | Aron nee Rosa et al. | 128/303.1 |
| 4,336,809 | 6/1982 | Clark | 128/303.1 |
| 4,370,540 | 1/1983 | Davis et al. | 219/121.6 |
| 4,409,979 | 10/1983 | Rouesel et al. | 606/17 |
| 4,427,872 | 1/1984 | Saunders | 219/121 LH |
| 4,456,811 | 6/1984 | Hella et al. | 219/121.74 |
| 4,461,294 | 7/1984 | Baron | 128/303.1 |
| 4,469,931 | 9/1984 | MacKen | 219/121 LG |

(List continued on next page.)

FOREIGN PATENT DOCUMENTS

| | | |
|---|---|---|
| 0083494 | 7/1983 | European Pat. Off. . |
| 0111060 | 6/1984 | European Pat. Off. . |
| 0224322 | 3/1987 | European Pat. Off. . |
| 224322 | 6/1987 | European Pat. Off. .......... 128/303.1 |
| 0228778 | 7/1987 | European Pat. Off. . |
| 0151869 | 11/1987 | European Pat. Off. . |
| 1040181 | 10/1954 | Fed. Rep. of Germany ...... 128/395 |
| 1288245 | 1/1969 | Fed. Rep. of Germany . |
| 3148748 | 7/1983 | Fed. Rep. of Germany .... 128/303.1 |
| 3801158 | 7/1989 | Fed. Rep. of Germany ...... 128/633 |
| 8701930 | 4/1987 | PCT Int'l Appl. . |

OTHER PUBLICATIONS

"Multiple Scattering . . . " by Cohen et al; IEEE Trans. on Biomed. Eng., vol. BME-23, No. 5, pp. 391–400, Sep. 1976.

(List continued on next page.)

*Primary Examiner*—David Shay
*Attorney, Agent, or Firm*—Morgan & Finnegan

[57] ABSTRACT

A method and apparatus for modifying corneal refractive properties includes a laser source and an ring-like deflector positioned about the cornea. The ring-like deflector is contoured and positioned about the cornea. The contour of the deflector is selected to affect the desired post-operative corneal curvature. A beam emitted from the laser source is deflected in a (predictable) controlled manner by the ring-like deflector at any desired point such that the beam strikes the cornea tangentially, ablating or lathing the contacted corneal surface. A masking device or an axicon can be provided in cooperation with a wide-body laser beam to deliver a ring of laser light to the deflector causing the light to strike the cornea tangentially in a ring-like pattern substantially centered about the visual axis. Alternatively, in a narrow-beam embodiment, the beam may be translated in the radial direction and revolved about the visual axis or rotated off parallel to the visual axis causing the beam to be deflected off of the ring-like deflector for striking the cornea tangentially over 360°.

10 Claims, 12 Drawing Sheets

U.S. PATENT DOCUMENTS

| | | |
|---|---|---|
| 4,533,812 | 8/1985 | Lorenz .......................... 219/121 LH |
| 4,551,608 | 11/1985 | Opower ........................ 219/121 LQ |
| 4,563,565 | 1/1986 | Kampfer ........................ 219/121 LJ |
| 4,638,801 | 1/1987 | Daly et al. ........................ 128/303.1 |
| 4,648,400 | 3/1987 | Schneider et al. ............... 128/303.1 |
| 4,665,913 | 5/1987 | L'Esperance, Jr. .............. 128/303.1 |
| 4,669,466 | 6/1987 | L'Esperance .................... 128/303.1 |
| 4,676,790 | 6/1987 | Kern ....................................... 623/5 |
| 4,678,422 | 7/1987 | York .................................. 425/174.4 |
| 4,694,828 | 9/1987 | Eichenbaum .................... 128/303.1 |
| 4,712,543 | 12/1987 | Baron ............................... 128/303.1 |
| 4,718,418 | 1/1988 | L'Esperance, Jr. .............. 128/303.1 |
| 4,721,379 | 1/1988 | L'Esperance ....................... 351/212 |
| 4,722,337 | 2/1988 | Losch et al. ...................... 128/303.1 |
| 4,724,452 | 2/1988 | Belgorod ............................. 364/415 |
| 4,729,372 | 3/1988 | L'Esperance, Jr. .............. 128/303.1 |
| 4,732,148 | 3/1988 | L'Esperance, Jr. .............. 128/303.1 |

OTHER PUBLICATIONS

"The Axicon: A New Type of Optical Element", pp. 592–597, Journal of Optical Society of America, vol. 44, No. 8 (1954), McLeod.

"Ring Pattern of A Lens–Axicon Doublet Illuminated By a Gaussian Beam", Applied Optics, Belenger and Rious, vol. 17, No. 7 (1978), p. 1080.

"Linear, Annular, and Radial Focusing with Axicons and Applications to Laser Machining", Applied Optics, Rioux, Tremblay and Belanger, vol. 17, No. 10 (1978).

"Far–Ultraviolet Laser Ablation of Atherosclerotic Lesions", Lasers in Surgery and Medicins, Linsker, 4:201–206 (1984), p. 201.

"Comparison of the Effects of Argon Fluoride (ArF) and Krypton Fluoride (KrF), Excimer Lasers on Ocular Structures", International Ophthalmology, (1985) Payman.

"Corneal Incisions Produced With the Fourth Harmonic (266 nm) of the YAG Laser", Lasers in Surgery and Medicine, Berns and Gaster, (1985), vol. 5, pp. 371–375.

"Endoexcimer Laser Intraocular Ablative Photodecomposition", American Journal of Ophthalmology, Pellin pp. 483–84 (Apr. 1985).

"Excimer Laser Therapy for Experimental Candida Keratitis", American Journal of Ophthalmology, Serdarevic, (1985) 99:534–538.

"Interaction of Ultraviolet Laser Light with the Cornea" Investigative Ophthalmology & Visual Science, Krueger, vol. 26 (1985), pp. 1455–64.

"Keratorefractive Surgery with the Excimer Laser" American Journal of Ophthalmology, Aron-Rosa, vol. 100, pp. 741-2, 1985.

"Quantitation of Corneal Ablation by Ultraviolet Laser Light" Archives of Ophthalmology, Krueger, vol. 103, pp. 1741-2 (1985).

"Effects of XeCL Excimer Laser on the Eyelid and Anterior Segment Structures" Archives of Ophthalmology, vol. 104, pp. 118–122 (1986).

"Excimer laser surgery of the cornea: Qualitative and quantitative aspects of photoablation according to the energy density", Journal of Cataract and Refractive Surgery, Aron–Rosa, vol. 12, pp. 27–34 (1986).

Preliminary Report on Corneal Incisions Created by a Hydrogen Fluoride Laser" American Journal of Ophthalmology, Loertscher, vol. 102, (1986) pp. 217–221.

"Laser Interactions With the Cornea", Survey of Ophthalmology, Krauss, vol. 31, (1986) pp. 37–53.

"In vivo Experiments with the Excimer Laser—Technical Parameters and Healing Processes", Ophthalmologica, Wollensak, (1986) vol. 192, pp. 65–69.

"A comparative study of corneal incisions induced by diamond and steel knives and two ultraviolet radiations from an excimer light", British Journal Of Ophthalmology, Marshall, (1986) vol, 70, pp. 482–501.

"A New Laser for Collagen Wounding in Corneal and Strabismus Surgery: A Preliminary Report", Transactions of the American Ophtho Society, Troutman, (1986).

"Preliminary Report on Corneal Incisions Created by a Hydrogen Fluoride Laser", American Journal of Ophthalmology, Loertscher, (1986) vol. 102, pp. 217–221.

"Corneal Endothelial Injury in Rabbits Following Excimer Laser Ablation at 193 and 248 nm", Archives of Opthalmology, Dehm. (1986 vol. 104, pp. 1364–1368.

Dynamics of the Ultraviolet Laser Ablation of Corneal Tissue", American Journal of Ophthalmology, Srinivasan, (1967) vol. 103, pp. 470–471.

"Excimer Laser Cut Lenticules for Epikeratophakia", American Journal of Ophthalmology, Lieurance, (1987) vol. 103, pp. 475–76.

"A Rotating Slit Delivery for Excimer Laser Refractive" American Journal of Ophthalmology, Hanna (1987) vol. 103, p. 474.

"An Ophthalmic Excimer Laser for Corneal Surgery: American Journal of Ophthalmology, Schroder (1987) vol. 103, pp. 472–473.

(List continued on next page.)

OTHER PUBLICATIONS

"Corneal Wound Healing After Excimer Laser Keratotomy in a Human Eye", American Journal of Ophthalmology, Aron-Rosa, (1987), vol. 103, pp. 454–464.

"Ultrastructural Comparison of Conventional Surgical and Argon Fluoride Excimer Laser Keratectomy", American Journal of Ophthalmology, Kerr-Muir, (1987) vol. 103.

"High-Speed Photography of Excimer Laser Ablation of the Cornea", Archives of Ophthalmology, Puliafito, (1987) vol. 105, pp. 1255–59.

"Noncontact Trephination of the Cornea Using a Pulsed Hydrogen Fluoride Laser", American Journal of Ophthalmology, Loertscher, (1987) vol. 104, pp. 471–475.

"Photorefractive Keratectomy: A Technique for Laser Refractive Surgery" Journal of Cataract & Refractive Surgery", Munnerlyn, (1988) vol. 14, pp. 46–52.

"Mutagenic Potential of a 193-nm Excimer Laser on Fibroblasts in Tissue Culture", Ophthalmology, Trentacoste, (1987) vol. 94, pp. 126–128.

"Excimer Laser Keratectomy for Correction of Astigmatism" American Journal of Ophthalmology, Seiler, (1988) vol. 105, pp. 117–174.

"Excimer Laser Keratectomy for Myopia With a Rotating-Slit Delivery System" Archives of Ophthamology, Hanna, (1988), vol. 106, pp. 245–250.

"Excimer Laser Trephination in Penetrating Keratoplasty", Ophthalmology, Serdarevic, (1988) vol. 95, pp. 493–505.

Laser and Elektrooptik, vol. 10, No. 1, Mar. 1978, Patiki, et al.

Advanced Techniques in Ophthalmic Microsurgery, vol. 2, Girard, pp. 84, 107–110, 114, 116, 123, 125–133 and 143–171 (Mosby, 1981).

"Thermokeratoplasty . . . ", Investigative Opthomology, Mar. 1974, Shaw and Gasset.

"A Technique for Selective Heating . . . ", Investigative Ophthamology and Visual Science, (1975), Dos and Albillar.

"Extreme Sensitivity in the Corneal Epithelium to Far Ultraviolet ArF Excimer Laser Pulses," Taboada and Archibald.

Ophthalmic Lasers, Second Edition, (Mosby 1983) L'Esperance, pp. 8–27.

"Response of the Corneal Epithelium to KrF Excimer Laser Pulses, Health Physics, Taboada, vol. 40, pp. 677–683, 1981.

"Excimer Laser Surgery of the Cornea" American Journal of Ophthalmology, Trokel, vol. 96, pp. 710–715, 1983.

"Excimer Laser Radial Keratotomy" Ophthalmology, Cotliar, vol. 92, pp. 206–208, 1985.

"Excimer Laser Ablation of the Corneal and Lens" Ophthalmology, Puliafito, vol. 92, pp. 741–748, 1985.

"An Ultrastructural Study of Corneal Incisions Induced by an Excimer Laser at 193 nm", Ophthalmology, Marshall, vol. 92, pp. 749–758, 1985.

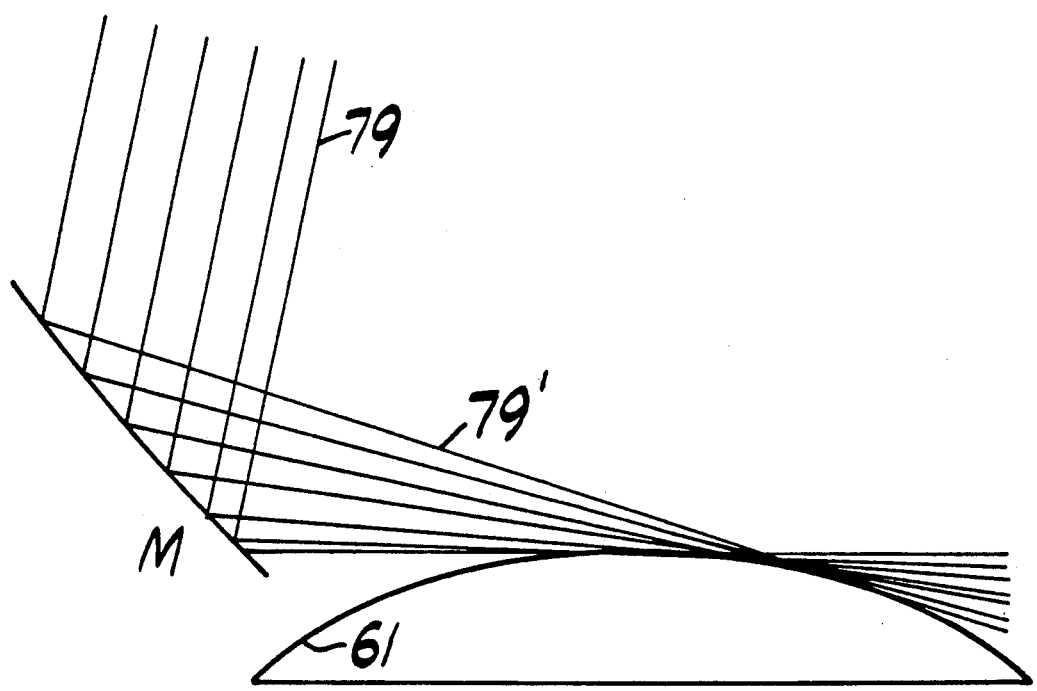
FIG. IIA
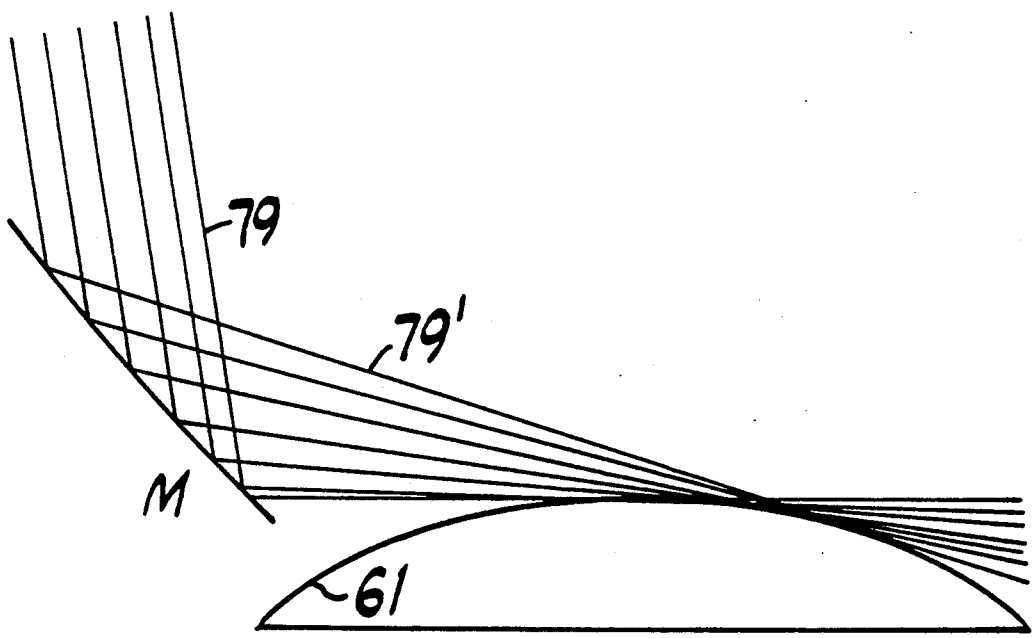
FIG. IIB

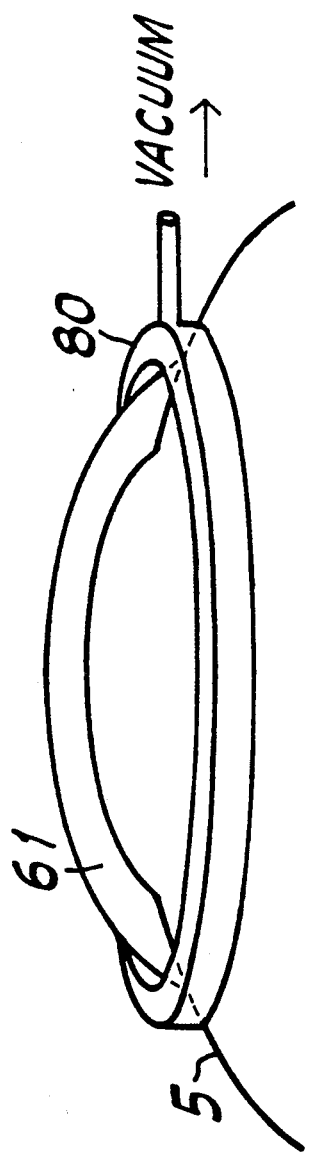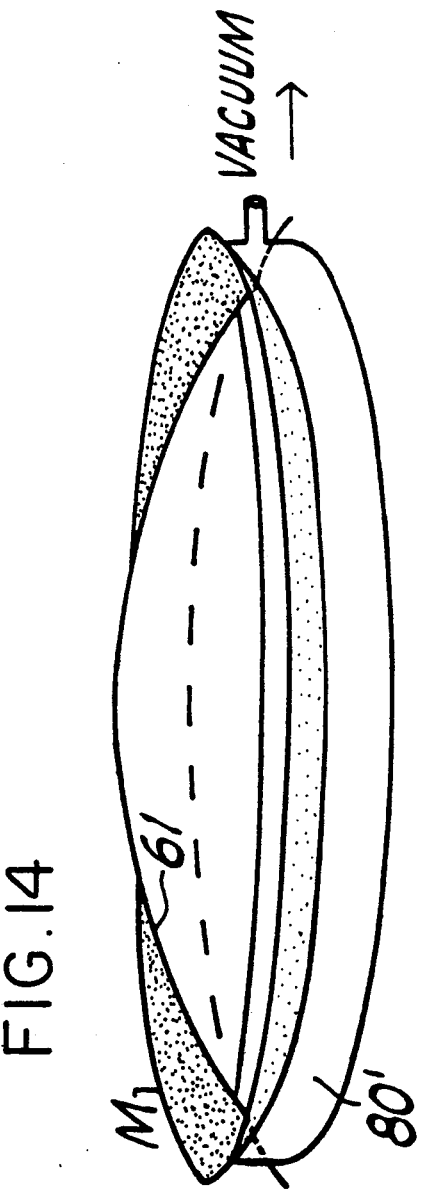

METHOD AND APPARATUS FOR MODIFICATION OF CORNEAL REFRACTIVE PROPERTIES

This is a continuation of co-pending application Ser. No. 07/184,222, filed on Apr. 22, 1988.

BACKGROUND OF THE INVENTION

The invention pertains to methods and apparatus for modifying the refractive properties of the eye. More particularly, the invention pertains to methods and apparatus for correcting refractive errors by modifying the cornea of the eye.

In general terms, the human eye functions by sensing light rays. Such light rays tend to be focused as they pass through the cornea, the aqueous humor, the lens and the vitreous humor. Ideally, the focal point of light, after passing through these components, will be at the retina. Emmetropia, or the lack of refractive error, is thus characterized by the focal point of the light entering the eye from an infinite distance and falling on the retina.

FIG. 1 illustrates the condition of emmetropia. As shown in FIG. 1, light enters the eye through the cornea 61 and passes through the cornea, the aqueous humor 2, the crystalline lens 3 and the vitreous humor 6. The light is focused by the refractive power of the cornea 61, the aqueous humor 2, the crystalline lens 3 and the vitreous humor 6 to a focal point P1 which, in the case of emmetropia as shown in FIG. 1, is at the retina 4. The globe of the eye is generally indicated at numeral 5 in FIG. 1.

Billions of human beings suffer impaired vision due to refractive errors of the eye characterized by the focal point of light failing to be at the retina, but rather falling short of or behind the retina. Common refractive errors of the eye fall into three main categories: myopia, hyperopia, and astigmatism. Myopia (FIG. 2), also known as nearsightedness, results when the focal point P2 of the eye is located anterior to the retina 4. Hyperopia (FIG. 3), also known as farsightedness, results when the focal point of the eye is located posterior to the retina 4. Astigmatism results when the eye has different refractive errors at different meridians. Thus, astigmatism may be present as a combination of any two of emmetropia, myopia and hyperopia in the same eye. For example, in an astigmatic eye, light entering the eye in a horizontal meridian may be focused anterior to the retina, while light entering the eye in a vertical meridian may be focused posterior to the retina.

As is well known, the cornea provides approximately two-thirds (⅔) of the refractive power of the eye. This is primarily due to the optically powerful air/cornea interface created by the large disparity of refractive indices between the air (1.00) and the cornea (approximately 1.37). The aqueous/lens interface causes further refraction within the eye.

Because the cornea is such an important factor in refraction of the eye, a wide variety of method and apparatuses have been applied in the past to alter the cornea in an effort to eliminate refractive errors. For example, contact lenses, which are also commonly used as refractive entities in themselves, have been intentionally malfitted to temporarily alter the corneal curvature. The latter technique is known as "orthokeratology" and generally results in only a temporary change in the corneal curvature. Orthokeratology has a further deficiency in that it is known to induce potentially serious corneal inflammation and scarring.

Several other techniques are known for altering the cornea in various ways to compensate for refractive errors of the eye. For example, radial keratotomy involves the making of radially orientated slit-like incisions in the cornea, in various patterns, to attempt to correct myopia and/or astigmatism. At present, however, the results of radial keratotomy are unpredictable and are often not reproducible in the same patient. Additionally, it is as yet unclear how long the results of radial keratotomy last. Further, there have been reports of corneal degenerations, infections and distortions after radial keratotomy, such conditions obviously having the potential for serious visual loss.

It is also known to use lasers for altering the condition of the cornea. U.S. Pat. No. 4,461,294 illustrates the use of the thermal effect of a laser to induce corneal-recurving scars by imbedding, under pressure, light absorbing colored bodies in the cornea in a radial pattern. The colored bodies in the cornea are exposed to a thermal laser through a matched, slitted diaphram In the technique disclosed by the U.S. Pat. No. 4,461,294, corneal tissue is burned for the purpose of creating scar tissue Another technique for modifying the cornea, known as lamellar keratoplasty involves the taking of a slice of a patient's cornea, or a donor's cornea, freezing the portion and lathing it in a hard-frozen state to a new curvature prior to suturing onto the eye of the patient. Particular methods employing this technique include keratomileusis, keratophakia, and epikeratophakia, each of which requires cutting and suturing of the patient's cornea.

Yet another cornea modification technique is disclosed in U.S. Pat. No. 4,665,913 which discusses a device for exposing the cornea to an excimer laser in perpendicular fashion to reshape the cornea. The U.S. Pat. No. 4,665,913 patent discloses a laser which is directed at the eye substantially along the visual axis of the eye. Removal of tissue is effected by exposing the cornea head-on to varying flux densities and exposure time in either rectilinear or spiralling fashion. This head-on exposure to the radiation of the laser would presumably expose the eyes delicate internal structures, such as the iris, the lens and the retina, to potentially damaging levels of radiation. Additionally, in such a device, if the output of the laser were inadvertently increased, deeper levels of tissue penetration could result in accidental perforation of the cornea or irregular corneal refracting surfaces.

In U.S. Pat. No. 4,724,522 (Feb. 9, 1988), which is hereby incorporated-by-reference, I describe methods and apparatus for improving corneal refractive properties, these methods and apparatus providing tangential striking of the cornea with a laser beam. FIG. 6 herein is a partial elevational view of one embodiment of a laser delivery device according to U.S. Pat. No. 4,724,522. Shown in FIG. 6, positioned about a human eye 5 including cornea 61, are a laser beam 79, and a variable, optical element $M_3$. FIG. 6 demonstrates six representative positions of optical element $M_3$, namely $M_{3A-F}$. In the practice of the embodiment of FIG. 6, the positions $M_{3A-F}$ would be calculated to result in the ablating beam touching the cornea tangentially at different positions to effect a new anterior corneal curvature.

Suggested surgical procedures for modifying corneal refractive properties in treating the conditions of myopia and hyperopia with an apparatus according to my earlier invention of U.S. Pat. No. 4,724,522 are described by way of reference to FIGS. 4A, 4B and 5 herein. FIGS. 4A, 4B and 5 illustrate schematic cross-sectional views of the eyes of a myopic correction (FIG. 4A with a smaller optical zone and FIG. 4B with a larger optical zone) and a hyperopic correction (FIG. 5). In FIGS. 4A, 4B and 5, $RC_I$ depicts the initial or pre-operative corneal radius of curvature, RCF depicts the final or post-operative corneal radius of curvature, $T_I$ depicts the initial or pre-operative corneal thickness and $T_F$ depicts the final or post-operative corneal thickness.

For treatment of the myopic patient (FIG. 4A), corneal tissue 40 may be removed from the apex 41 outward to the periphery 42, or from the periphery inward to the corneal apex, altering the cornea from its initial corneal thickness $T_I$ and initial corneal radius of curvature $RC_I$ to a lessened final corneal thickness $T_F$ and an increased final corneal radius of curvature $RC_F$. Treating myopia (FIG. 4A) in such a procedure should thus result in a flatter cornea. FIG. 4B demonstrates the same $RC_F$ but with a larger optical zone diameter 43'.

In correcting or treating hyperopia (FIG. 5), the resultant corneal radius of the curvature should be smaller, resulting in a steeper cornea. Thus, in treating the hyperopic patient, the corneal radius of curvature and corneal thickness are both reduced as corneal tissue 50 is removed primarily from the mid-pheriphery 52 as illustrated in FIG. 5.

It is an object of this invention to provide an alternative method and apparatus for accurately shaping the cornea to compensate for refractive errors of the eye.

It is a further object of the invention to provide a method and apparatus for reshaping the cornea of the eye in vivo or in vitro without the need for removing and then suturing the corneal tissue.

It is a further object of the invention to provide a method and apparatus for shaping the cornea of the eye in which there is no necessity for freezing the corneal tissue prior to shaping but which may be used in conjunction with freezing techniques.

It is a still further object of the invention to provide a method and apparatus for shaping the cornea which reduces or eliminates the risk of accidental damage to the cornea and the other components of the eye, such as the iris, the lens and the retina.

It is a still further object of the invention to provide a method and apparatus which meets the foregoing objectives and which is safe, predictable, and reproducible.

SUMMARY OF THE INVENTION

These and other objects of the invention are met by providing a method and apparatus for reshaping the cornea of the eye, including a laser or other high intensity electromagnetic radiation source and a fixed, precisely contoured ring-like deflective member positioned about the cornea of the eye. Laser light, emitted from the laser source, is deflected by the ring-like deflective member to tangentially strike the cornea of the eye, causing controlled corneal ablation and thereby modifying the radius of curvature of the cornea. The contoured portion of the ring-like deflector should provide a pre-selected curve to effect the desired post-operative corneal curvature. A wide-body laser beam may be used in cooperation with a masking device or axicon to provide a ring of laser light to the deflector. Alternatively, a narrow laser beam may be tracked circularly around and linearly across the ring-like deflector to effect the desired ablation pattern.

In utilizing a ring-shaped, fixed deflector as the aiming deflector, the invention provides the advantage of reducing the number of moving parts as compared with devices which require a translating and rotating element as the aiming element.

With the invention, the cornea is lathed tangentially in either its natural or frozen state, in vivo or in vitro, in an area centered about its optical axis and encompassing its optical zone by either a non-thermal emission such as an ultraviolet or excimer laser, or a thermal emission such as an infra-red laser, under automated or manual control. The invention is effective to modify the corneal curvature and thereby its refractive properties by shaving or vaporizing part of the optical zone of the cornea in a precisely calibrated and predictable manner, eliminating the need for cutting blades or mechanical lathing which were heretofore provided. The invention also obviates the need for suturing and scarring of the cornea. In addition, since the laser beam strikes the cornea only tangentially, changes in the frequency or power output of the laser would not carry the risk of perforation, and delicate intraoccular structures would not be at risk for direct exposure to the laser.

BRIEF DESCRIPTION OF THE DRAWINGS

The invention will be described in greater detail below by way of reference to the following drawings, in which:

FIGS. 11A and 11B illustrate a cross-section of element M being struck at angles other than parallel to the optical axis of the eye according to the invention;

FIG. 13 illustrates a method of fixing the eye in position prior to and during an operation according to the invention;

FIG. 14 illustrates an eye fixation device including a ring-like deflector according to the invention;

DETAILED DESCRIPTION OF THE DRAWINGS

Figure 7A:
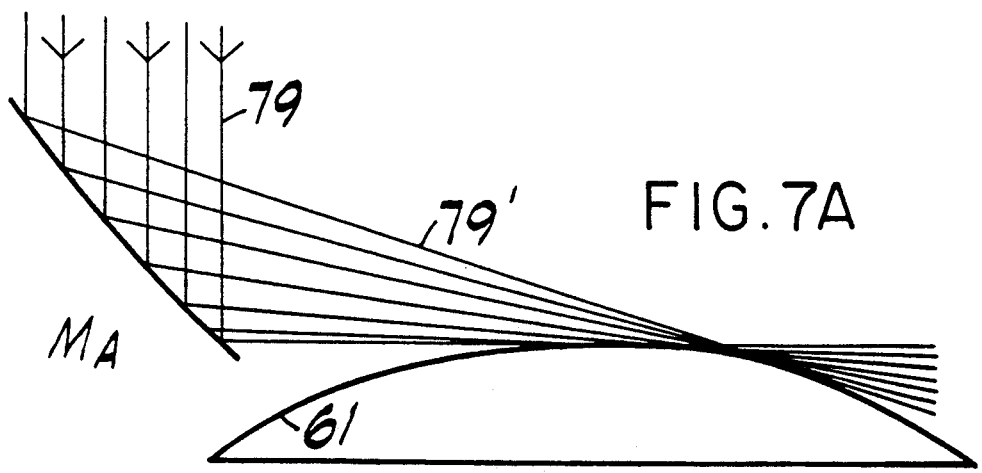
FIGS. 7A and 7B illustrate partial cross-sectional views of halves of potential elements MA and MB, encircling the cornea according to the invention.
Figure 7B:
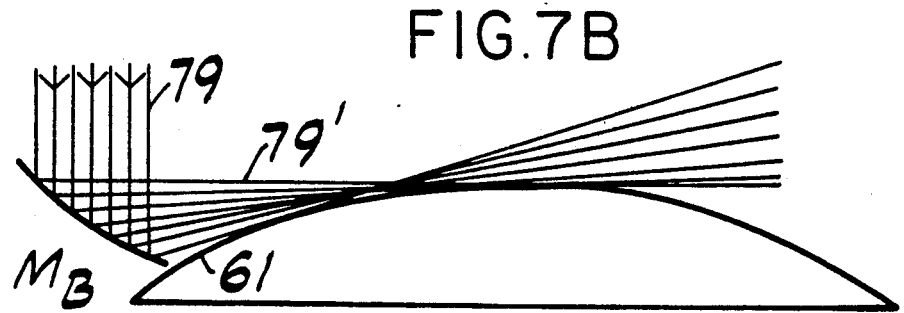

FIGS. 7A and 7B are partial, cross-sectional views showing halves of ring-like deflectors $M_A$ and $M_B$, respectively, encircling the cornea 61 in accordance with one embodiment of the invention. In the embodiment of FIG. 7A, the deflective element $M_A$ is constructed for positioning anterior to the corneal apex to effect tangential delivery of the beam. In the embodiment of FIG. 7B, the ring-like element $M_B$ is designed for positioning posterior to the corneal apex to effect tangential delivery of the beam.

FIG. 7A thus illustrates an embodiment of the invention wherein the deflective element $M_A$ is positioned with its deflective surface substantially anterior to the corneal apex. Element $M_A$ is contoured such that an ablating beam 79 hitting the surface of the deflector $M_A$ will be deflected (79') to be tangential to a portion of the desired, new, anterior corneal surface curvature. The manner of contouring element $M_A$ can be seen as the spatial summation of all possible positions $M_{3A-F}$ of the prior art device of FIG. 6, in a single element.

Figure 6:
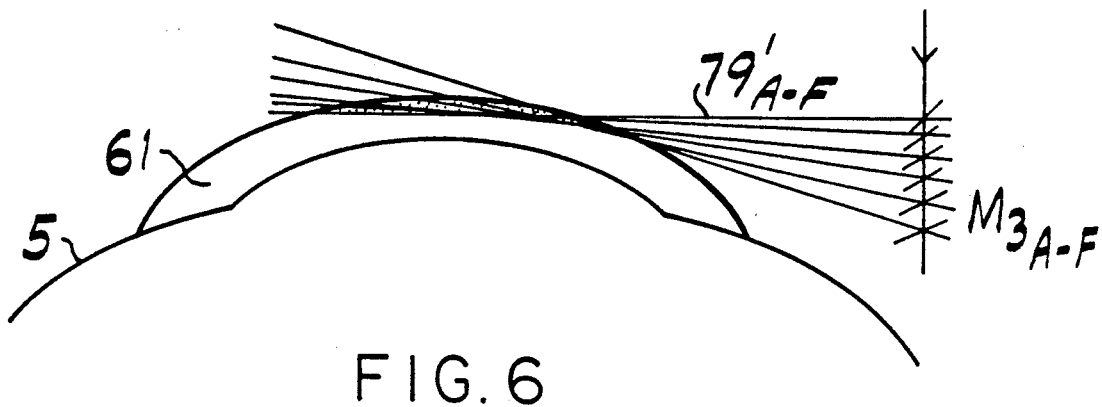
FIG. 6 demonstrates six representative positions of other optical element M3 described in U.S. Pat. No. 4,724,522 which could be used to ablate the cornea tangentially to create a new anterior corneal curvature.

The curved deflector $M_B$ of FIG. 7B is designed to be located substantially posterior to the corneal apex and may be similarly viewed as the summation of deflective positions $M_{3A-F}$ of prior art embodiment similar to FIG. 6 wherein the deflector is located substantially posterior to the corneal apex.

In the embodiments of FIGS. 7A and 7B, a different curve for element $M_A$ should be provided for each specific desired post-operative corneal curvature. Element $M_A$ and $M_B$ can be single elements that rotate about the cornea or could be embodied in a single, stationary, circumferential ring-like element. This element could be exposed to a thin or broad ablating beam via a rotating arm 59 and optics $M_1$, $M_2$ as seen in FIG. 8.

Figure 8:
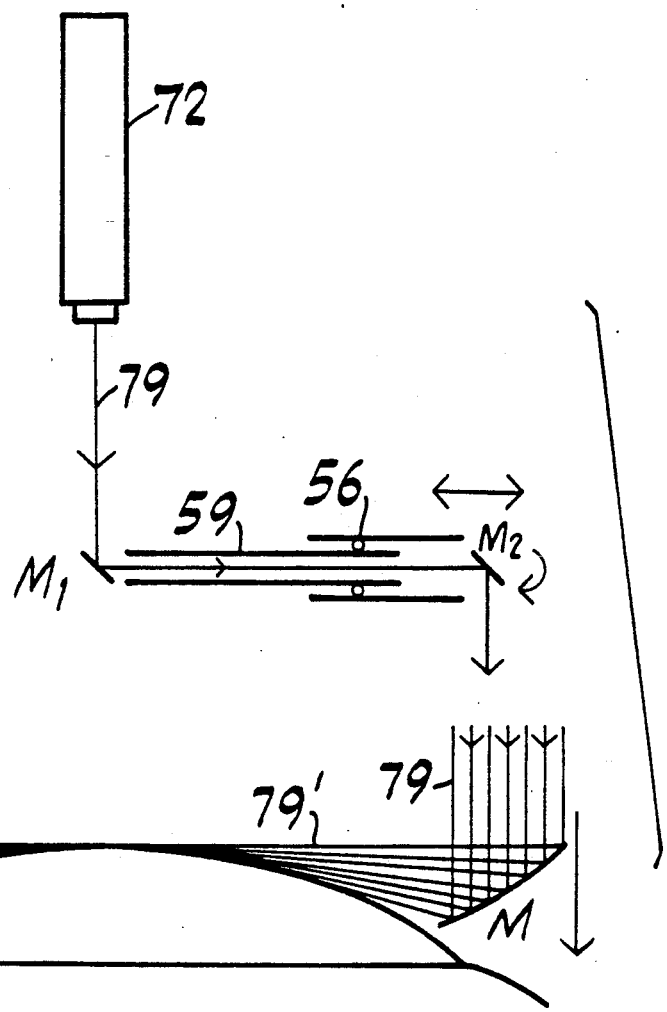
FIG. 8 illustrates a cross-sectional view of the cornea and ring-like deflector M being struck by light from a rotating arm delivery system according to the invention.

FIG. 8 illustrates a partial cross-sectional view of the cornea 61 and circular element M in accordance with another embodiment of the invention. Circular element M may be a spherical or aspherical element which, depending on the radial location of the area intercepted by the incident beam 79, may be seen as the spatial summation of all of the positions $M_{3A-F}$ of element $M_3$ in FIG. 6, placed in continuous fashion 360 degrees encircling the cornea 61.

Figure 9:
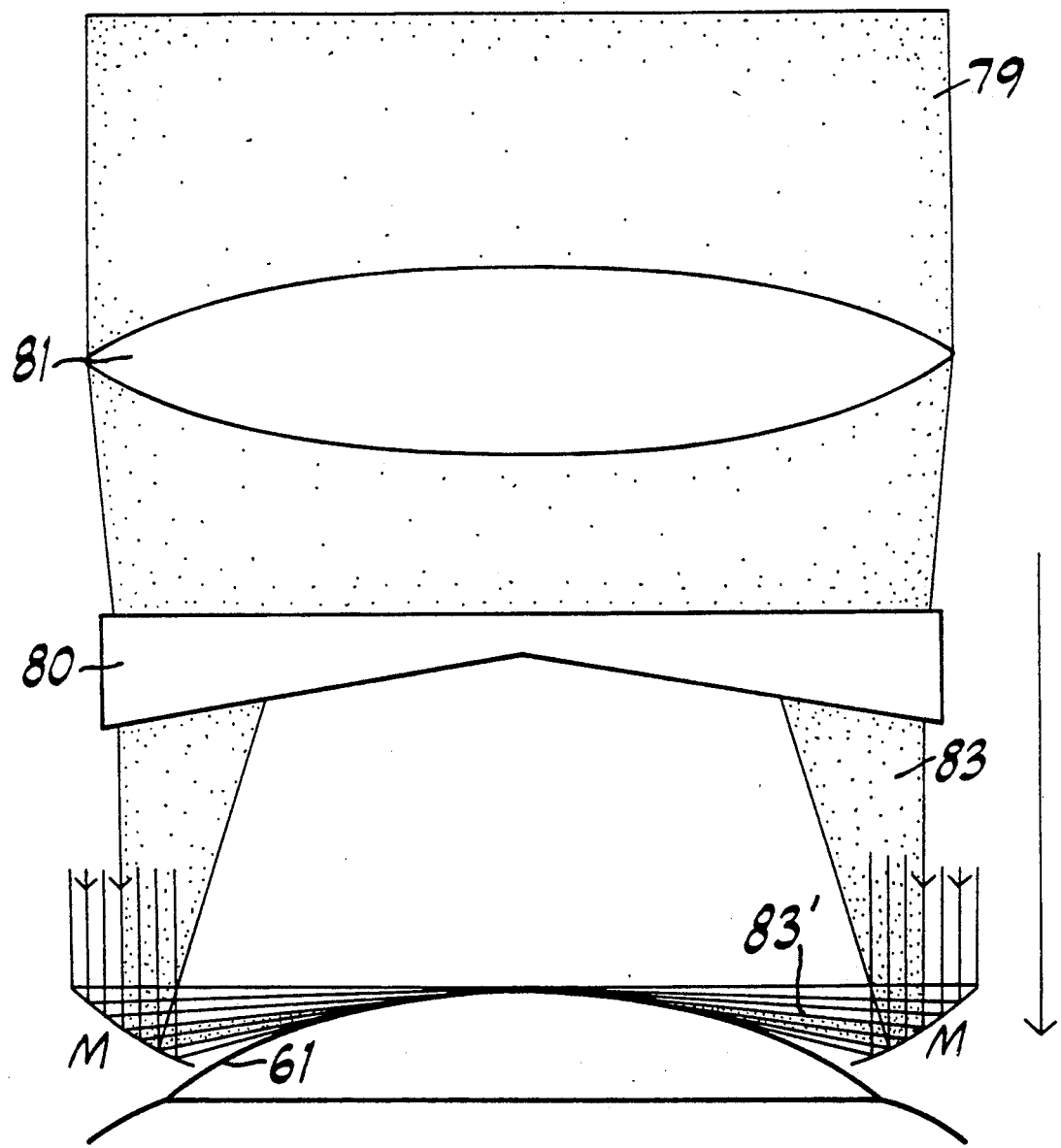
FIG. 9 illustrates the simultaneous striking of the ring-like element M in annular fashion according to the invention by a ring of light generated by an optical system containing an axicon element.
Figure 10:
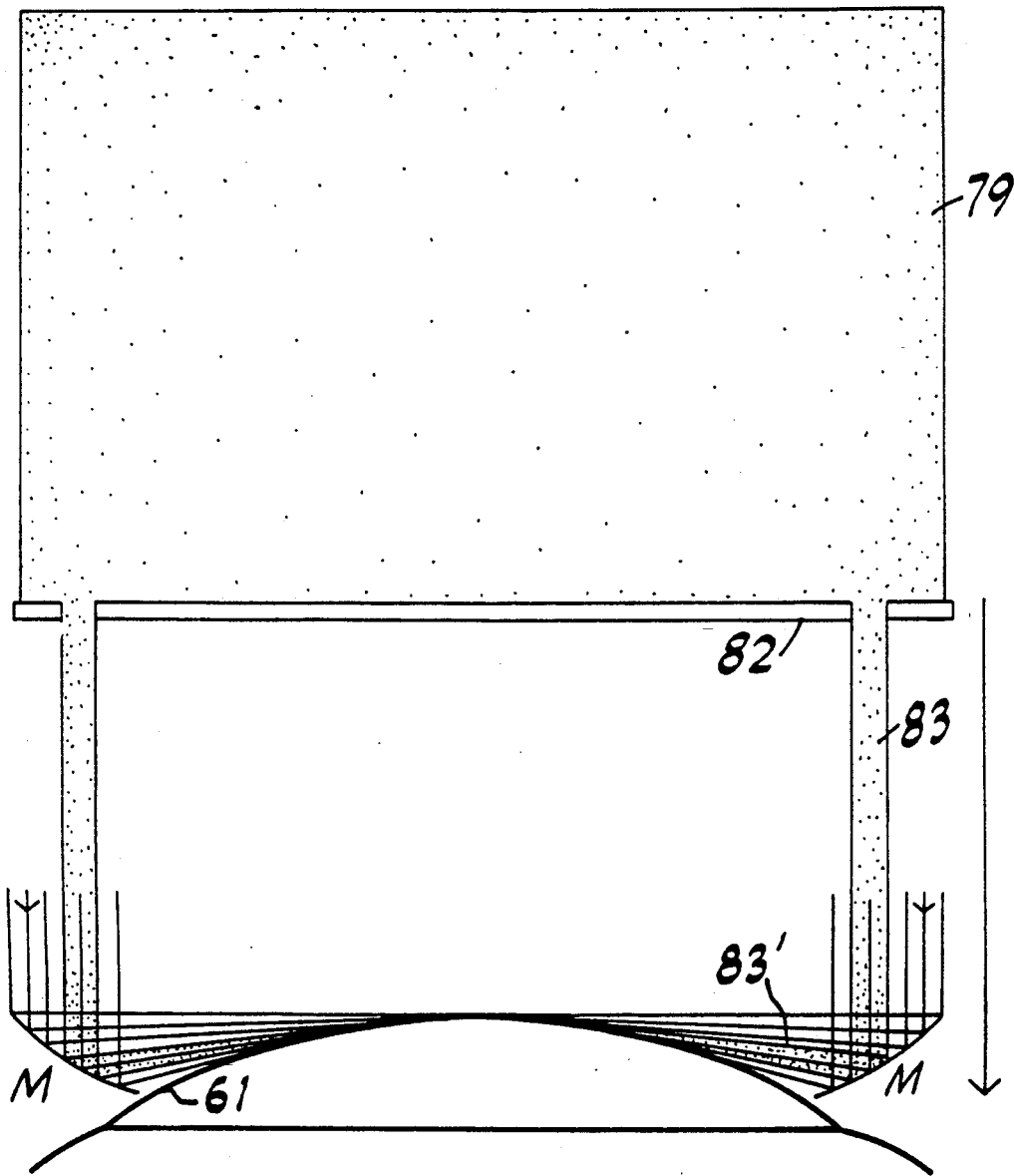
FIG. 10 illustrates the simultaneous striking of the ring-like element M in annular fashion according to the invention by a ring of light generated by an optical system using a masking device.

A thin or broad, highly collimated beam 83 can be presented to circular element M in annular (ring-like) fashion by optical elements such as an axicon 80 and lens 81 as seen in cross section in FIG. 9. A diaphram or other masking device 82, as seen in cross-section in FIG. 10, can also present a precisely collimated ablating beam 83 to the deflective element M.

Figure 4A:
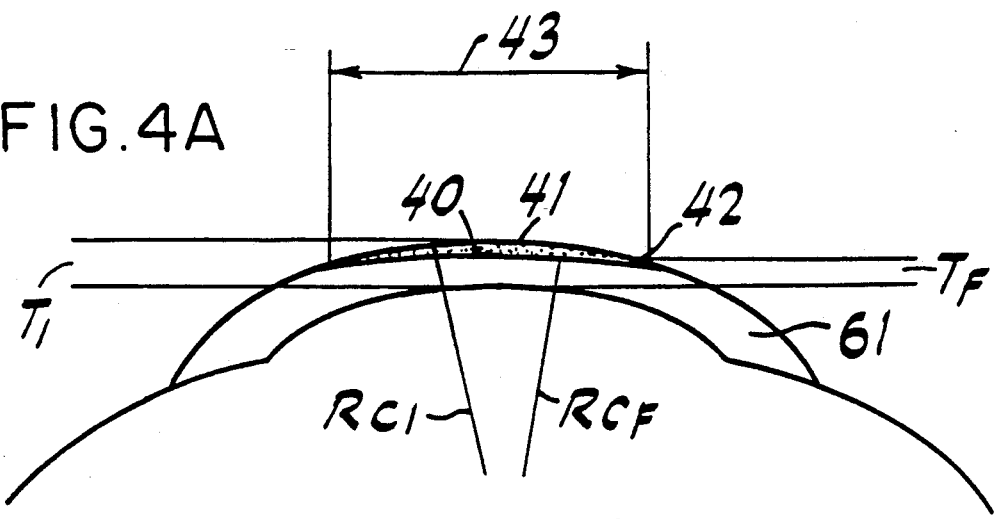
FIG. 4A illustrates the ablation of corneal tissue in the treatment of a myopic patient.
Figure 4B:
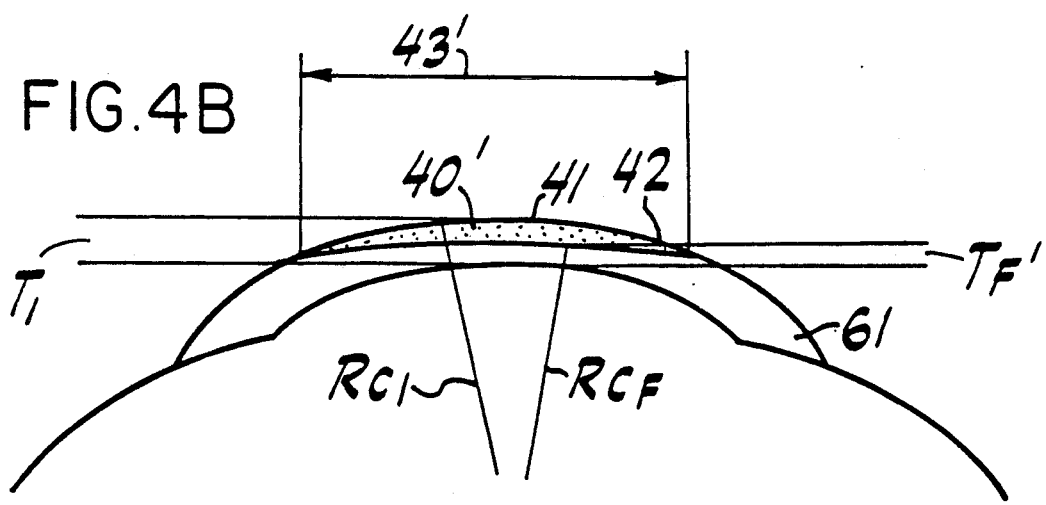
FIG. 4B illustrates the same myopic ablation correction pattern as FIG. 4A with an increased optical zone area.
Figure 5:
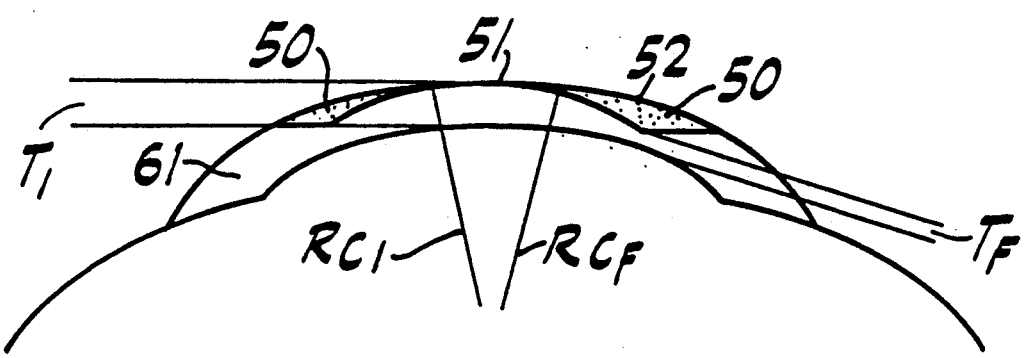
FIG. 5 illustrates the ablation of corneal tissue in the treatment of a hyperopic patient.

In order to result in the exact desired post-operative, non-astigmatic anterior corneal curvature, the thin or broad annulus (or ring) of light 83 processed from the ablating beam should strike substantially simultaneously about the same precisely curved radial location of the element M for 360° around the eye. Desired post-operative corneal profiles in the treatment of myopia and hyperopia are illustrated above by way of reference to FIGS. 4A, 4B and 5.

Figure 16:
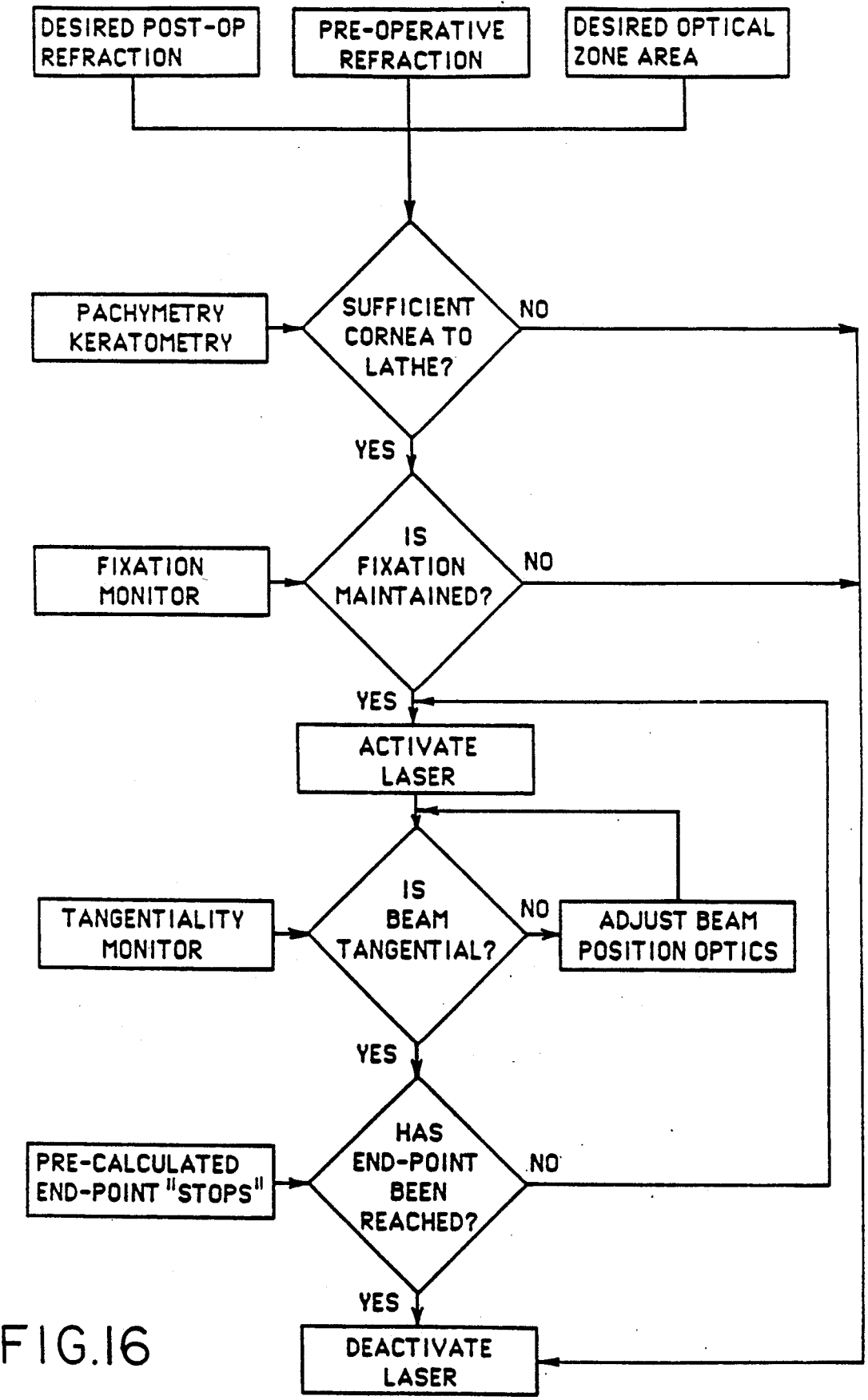
FIG. 16 is an operational flow chart describing the functioning of an apparatus according to one embodiment of the invention.

The desired optical zone area can be increased by positioning ring-like element M and its preceding optics (FIGS. 8, 9 and 10) progressively more posteriorly. To prevent perforation of the cornea, precise calculation of how much thickness of cornea will remain for a specific myopic or hyperopic ablation pattern, power correction and optical zone area can be calculated pre-operatively and monitored intra-operatively as shown in FIG. 16. Safety stops can be set manually or automatically to prevent excessive tissue removal.

Figure 18A:
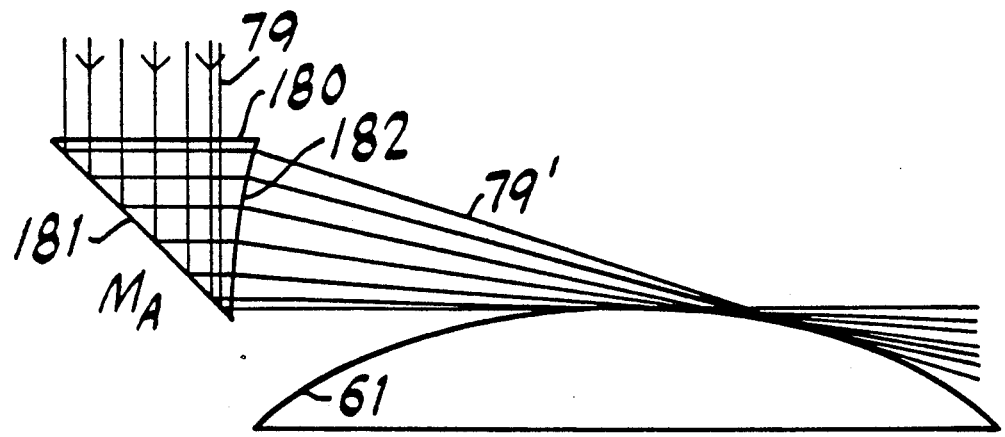
FIGS. 18A-18D illustrate alternative embodiments of the invention wherein the ring-like deflector is a prismatic device.
Figure 18B:
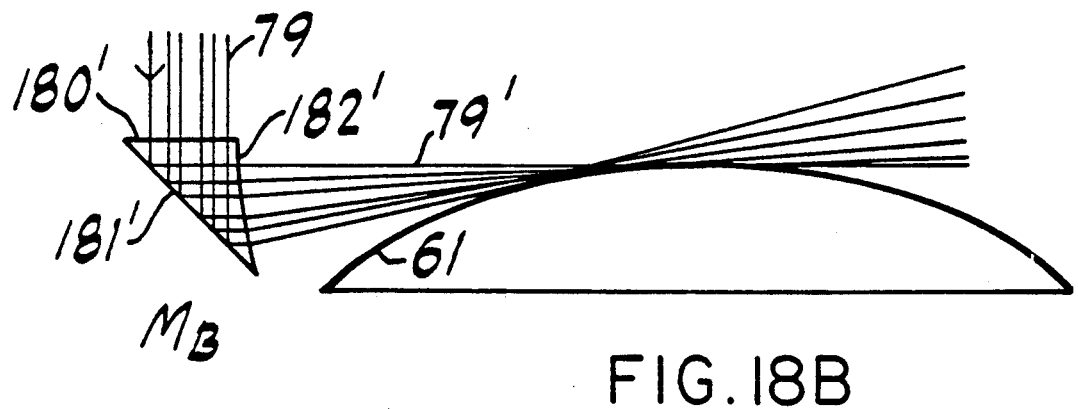

FIGS. 18A-18D illustrate alternative embodiments of the invention wherein the deflective element M is a prismatic device. FIG. 18A illustrates a partial cross-sectional view of a prismatic deflector $M_A$ having a curved side 182 contoured for positioning the deflector substantially anterior to the corneal apex. FIG. 18B illustrates a prismatic deflector $M_B$ having a curved surface 182' contoured for positioning the prismatic device substantially posterior to the corneal apex. Each of the prismatic deflectors $M_A$, $M_B$ of FIGS. 18A and 18B also include flat sides 180, 180, and 181, 181'. The incident beams 79 pass through the prismatic devices and are deflected (shown at 79') to strike the cornea 61 tangentially to affect the corneal curvature.

Figure 18C:
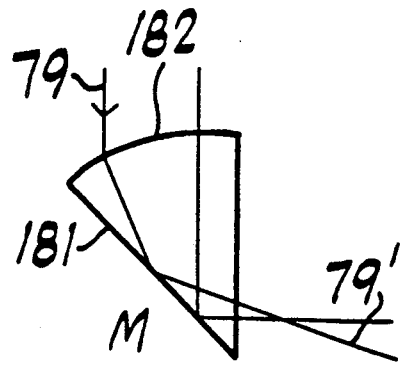
Figure 18D:
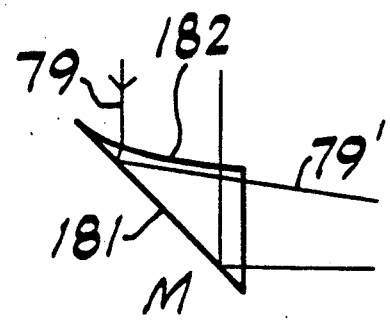

Similarly, a variety of flat, concave and/or convex sides may be provided within the prismatic deflector devices. For example, FIGS. 18C and 18D illustrate alternative embodiments wherein the incident beams pass through the contoured surfaces 182 and strike the straight back surfaces 181 prior to exiting as deflected beams 79'.

It should not be necessary for the ablating beam to parallel the optical axis of the eye, in practicing preferred embodiments of the invention. However, if the beam or its annular counterpart were to hit the curved element M on a diverging (or converging) angle relative to the eye's optical axis (FIGS. 11A and 11B), the curvature of element M would need to be curved specifically to create the desired optical correction via the desired tangential ablating beam geometry.

Figure 12A:
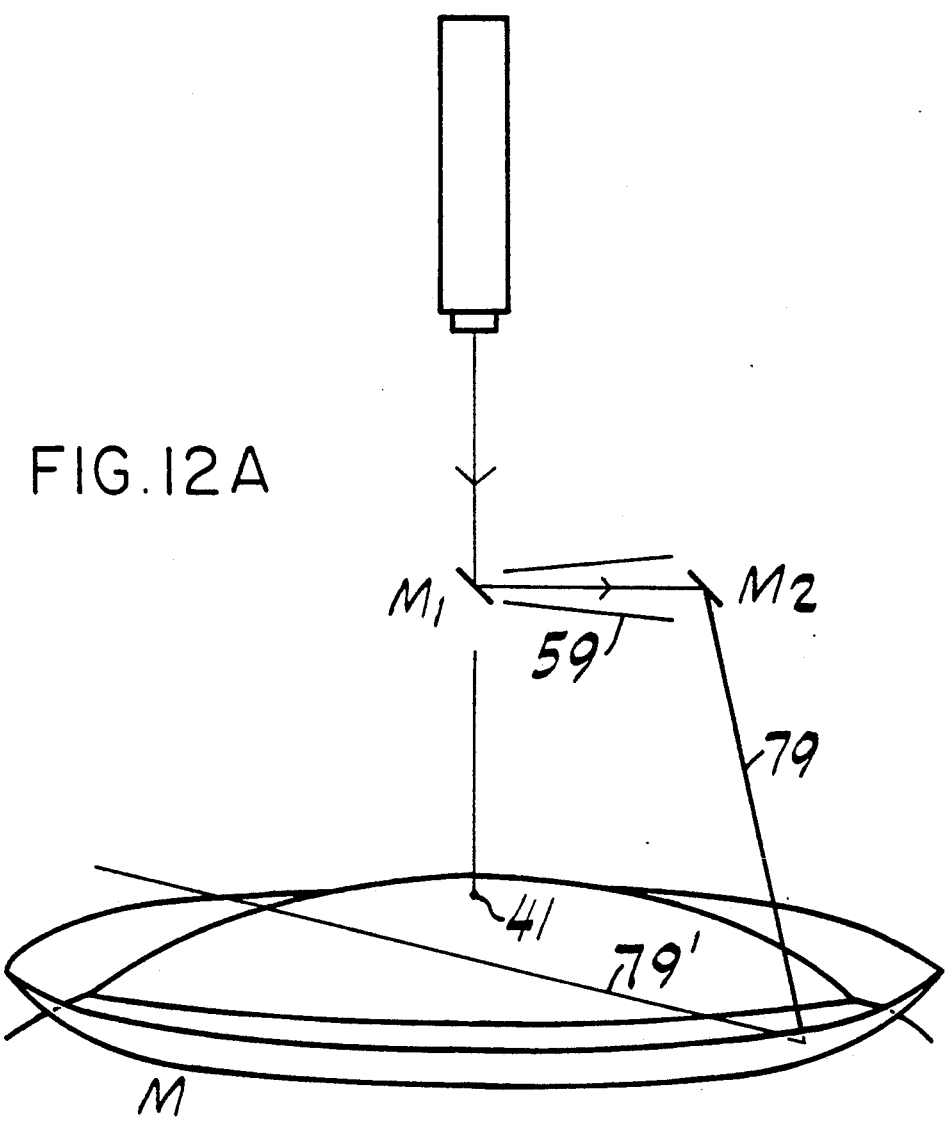
FIG. 12A illustrates a partial perspective view and FIG. 12B illustrates a plan view of a geometry for generating the correction of hyperopia according to the invention.
Figure 12B:
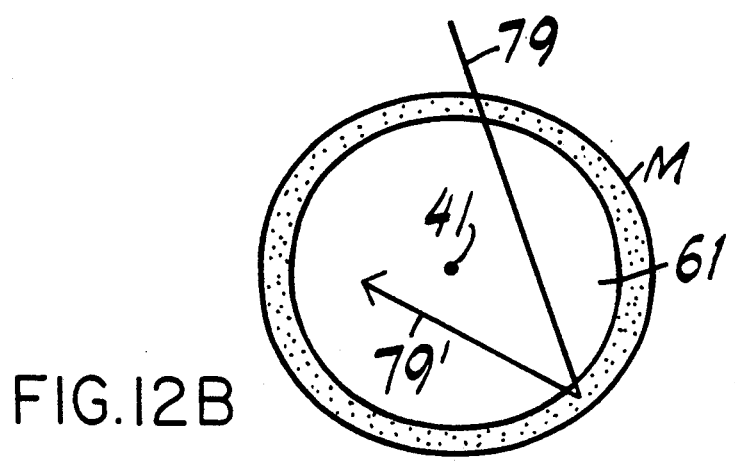

A special modification of ablating beam incidence is necessary to ablate a hyperopic correction via an annular deflector. An example of such a modification is illustrated in FIGS. 12A and 12B. In the embodiment of FIG. 12A, the beam would be delivered off-perpendicular in a precisely calculated and delivered fashion to be deflected off of deflector M in a non-radial fashion relative to the radius drawn from the optical center of the cornea to the deflector M. In this manner, the plane containing an incident (79) and deflected (79') ray of light would not contain the optical axis of the eye as shown in FIG. 12B.

My earlier U.S. Pat. No. 4,724,522, which is incorporated herein-by-reference, should be referred to in the practice of the instant invention, as it describes peripheral techniques applicable hereto, including presently preferred laser devices, complete monitoring of the surgical procedure and the incorporation of auto-refraction and light scatter monitoring to assure safety and efficiacy.

Referring again to FIG. 8, the rotating arm 59 may be hollow or comprised of fiber optic or other transmitting elements for transmitting the laser beam from the incident mirror $M_1$ to the intermediate mirror $M_2$. Arm 59 may rotate about the corneal axis to provide prescribed tangential lathing symmetrically about the entire circumference of the cornea 61. A slide 56 may be slidably mounted or otherwise secured to arm 59 to join in the rotating movement of the arm 59 about the optical axis of the cornea 61. The intermediate mirror $M_2$ may thus translate along arm 59 in cooperation with slide 56 and/or may pivot to direct the incident beam 79 to a different, predetermined radial location on element M or off-radial as shown in FIG. 12B.

Figure 15:
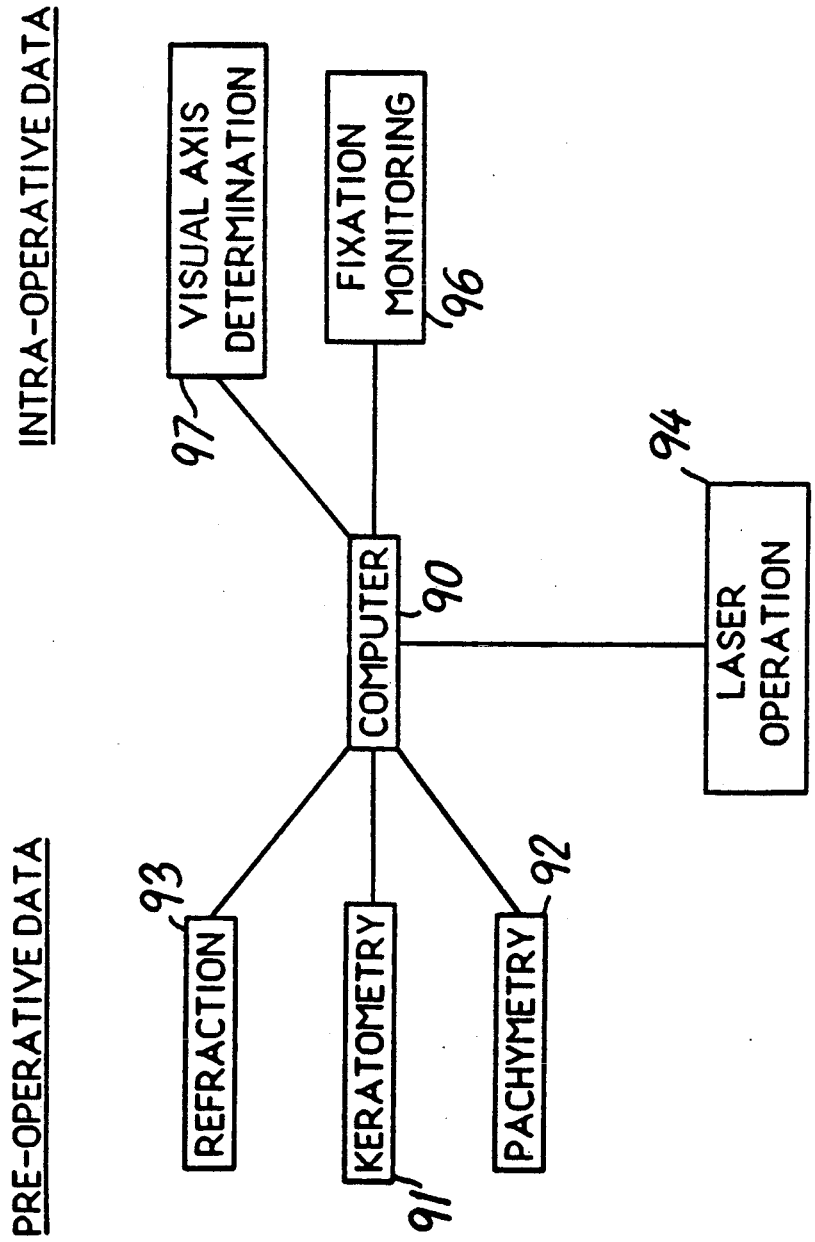
FIG. 15 is a control chart illustrating the functions of a command computer in an apparatus according to one embodiment of the invention.

The invention, in preferred embodiments, may include a variety of safety features as well as interactive efficiency monitors under computer control. As the corneal thickness will be altered in the treatments illustrated in FIGS. 4A, 4B and 5, it is important to determine pre-operatively how thick the cornea will be post-operatively, so as not to perforate the cornea while attempting to change its curvature. For this reason, referring to FIG. 15, pre-operative data of keratometry 91 (i.e., the corneal curvature) and pachymetry 92 (i.e., corneal thickness, "normal" being approximately 0.5 mm thickness at the corneal apex) are inputted into a system command computer 90. Data of refraction 93 (e.g., expressed in diopters) may also be determined pre-operatively and provided to the system computer controller. An autorefractor emitter and detector may be provided to interactively obtain refractive error conditions.

Figure 1:
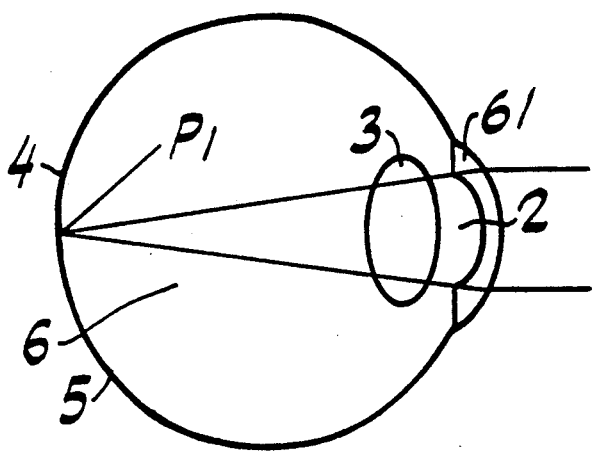
FIGS. 1-3 are schematic illustrations of human eyes illustrating the conditions of emmetropia, myopia and hyperopia, respectively.
Figure 2:
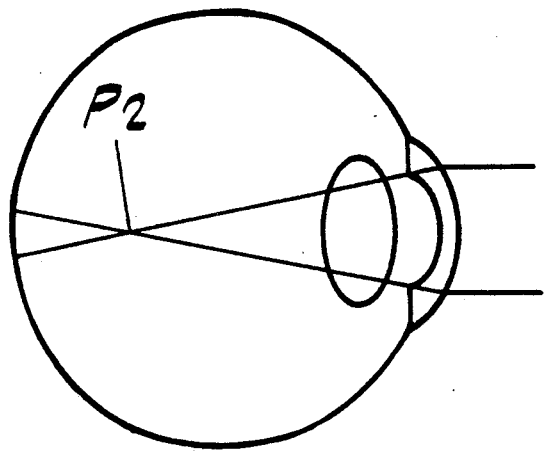
Figure 3:
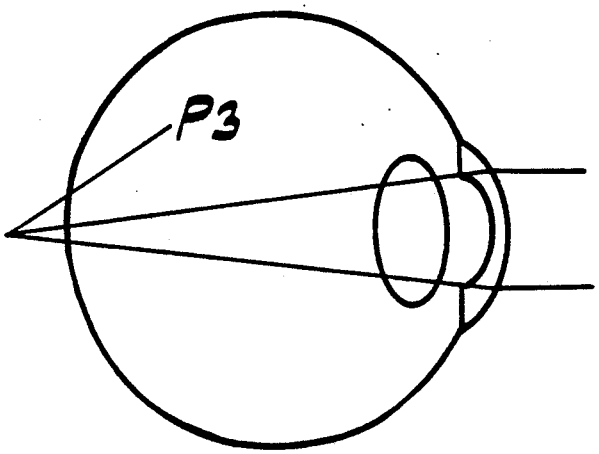

The computer 90 may be programmed to calculate whether the amount to be lathed off of the cornea to achieve the desired refractive correction exceeds the amount that would alter the structural integrity of, or perforate, the cornea. If the amount to be lathed exceeds a programmed safe amount, the computer 90 should not allow the system to commence laser operation 94. If the calculation proves lathing to be a viable option, laser operation 94 will be activated. During laser operation, the computer 90 may monitor, in real time, the visual axis 97 and the fixation 96 of the eye. In preferred embodiments, the surgical procedure will be done under constant guidance of the computer controller 90 to insure that the end-point (presumably emmetropia, FIG. 1) is not passed.

Additionally, the computer 90 may be adapted to operate the laser, including signalling of the laser 72 to emit the laser beam 79, and to control the frequency and speed of rotation of the arm 59, if necessary. It should be understood that the degree of lathing and the length of the lathing procedure may depend on various factors, such as: the desired corneal power correction, the desired optical zone area, the strength and the diameter of the laser beam, and, in certain embodiments, e.g. FIG. 8, the speed of arm rotation and the number of arm rotations required. Thus, accurate computer assistance will preferably be provided in an apparatus according to the invention to coordinate the variables and provide the appropriate calculations.

As FIG. 8 illustrates, the laser beam 79 is incident on mirror $M_1$, perpendicular to the corneal apex and exactly on the visual axis. In preferred embodiments of the invention, the visual axis of the patient will be determined automatically using a visual fixation device testing for either centration of corneal light reflexes or for the "red reflex" response to a collimated light beam entering the pupil, reflecting off the retina and exiting the pupil. In preferred embodiments, fixation will be closely monitored during the lathing procedure (see FIG. 15, item 96), such that if fixation along the visual axis is lost, the laser will automatically cease operation.

Throughout the procedure according to the invention, the globe 5 (see FIG. 1) of the eye should be precisely fixated. This may be accomplished by use of a known vacuum fixation ring 80 (FIG. 13) which may be attached to an X-Y axis movement device to automatically adjust the axis of fixation of the eye. An electronic output of such an X-Y axis movement device will preferably signal the control computer 90 (FIG. 15) to deactivate the laser source 72 (FIG. 8) upon detection of loss of fixation and should signal the computer when fixation has been re-established so that the lathing procedure can recommence.

In another preferred embodiment, shown in FIG. 14, the fixation device 80' can itself be devised to incorporate the curved, ring-like deflector surface of element M.

The deflector elements described herein may be fixed angle or curved mirrors or may be fabricated of a wide variety of non-mirror elements such as prisms, lenses, fiber-optic elements or holographic elements. Variable deflective elements are also contemplated.

Since the laser beam in an apparatus according to the invention is preferably maintained consistently tangential to the desired new corneal surface corneal surface, only the portion of the cornea that actually touches the beam is subject to ablation. Studies have indicated that precise control of the corneal cutting by an ultraviolet laser can yield negligible effects on corneal tissue immediately adjacent to the beams, yielding extremely precise effects.

Preferably, the laser source 72 (FIG. 8) of the invention will be a non-thermal laser such as an ultraviolet or excimer laser as described above. However, thermal or infra-red lasers can also be used. The ultraviolet lasers are currently preferred as they provide precise beams of energy which break apart protein bonds, ablating or vaporizing the cornea as opposed to burning the cornea as caused by thermal lasers. Of course, a wide variety of laser or other radiation sources may be provided within the spirit and scope of the invention.

Particularly preferred are ultraviolet lasers such as the excimer type of far-ultraviolet laser. Such lasers, charged with argon-fluoride gas, have been shown to precisely ablate corneal tissue at wavelengths of 193 nm. The laser output of such a laser may be pulsed with typical pulse energies of more than 300 mJ at a repetition rate of as much as 400 pulses per second. Alternatively, radiation from a frequency doubled or quadrupled Nd:YAG laser may be employed giving frequencies in the ultraviolet range.

Figure 17:
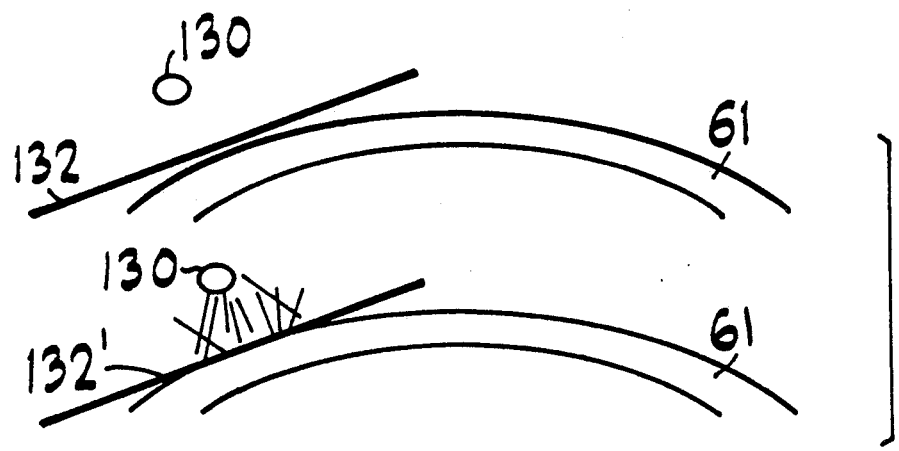
FIG. 17 illustrates the functioning of a light scatter detector used to determine tangentiality in one apparatus according to the invention.

As the light emitted from a laser is coherent, tangentiality can be monitored utilizing perpendicular light scattering techniques for detecting when a laser beam intersects the surface of the cornea tangentially. FIG. 17 illustrates the function of such a light scatter detector 130 which may be provided in an apparatus according to the invention so as to be in close proximity to the cornea 61 during operation of the invention. A first output signal may be provided by the light scatter detector 130 when laser beam 132 is in a non-tangential pattern relative to the cornea 61 and a second output signal may be provided to the computer when the laser beam 132' intercepts the cornea tangentially.

FIG. 16 illustrates the operation of an apparatus according to the invention. First, pre-operative refraction data is provided to the system computer to establish whether hyperopia or myopia is present and to determine how much refractive error to correct. Keratometry and pachymetry data are then provided to the computer to determine whether the patient has enough corneal tissue to safely carry out the lathing procedure. If not enough corneal tissue is available to safely carry out the procedure, then the operator will be so notified and the laser device will be disabled. Depending upon the pre-operative data, positions of the deflectors will be established. If suffcent corneal tissue is present, the computer may then be set to check that fixation has been maintained. If fixation has not been maintained, the laser will be disabled. If fixation is present, the laser will be activated. Note that at any time fixation is lost, the computer should automatically disable the laser.

While the laser is activated, the tangent monitor will be constantly operating to determine whether the laser is tangential to the cornea. If the laser is not tangential to the cornea, variable elements may be adjusted until tangentiality is achieved. Tangentiality may be constantly monitored through either system interrupts or polling procedures. Assuming tangentiality is achieved, and the laser lathing process is under way, the system will constantly monitor the status of the cornea until either emmetropia or a preset corneal contour is reached and at this point the laser will be deactivated.

The invention thus provides a method and apparatus for reshaping the cornea of the patent in vivo without the need for removing, reshaping and then suturing the modified corneal tissue back in place. In addition, with the invention, there is no need for freezing the corneal tissue prior to reshaping it, although the technique could easily be used with corneal tissue in the frozen state in conjunction with known lamellar keratoplasty techniques.

In the invention, radiant energy, from either a non-thermal laser such as an ultraviolet or "excimer" laser or a thermal laser such an an infra-red laser, can be used to modify the corneal curvature, and thereby its refractive properties, in vivo or in vitro to shave away or vaporize part of the optical zone of the cornea in a precisely calibrated and predictable manner. The invention obviates the need for blades for cutting or mechanical lathing and also obviates the need for suturing or unpredicably scarring the cornea of the patient as was required in various prior known methods. Additionally, since the incident laser beam touches the cornea only tagentially, rather than perpendicularly, changes in the lasers power output would not carry the risk of perforation of the cornea, as there would be no additional tissue in the path of the beam to be further exposed to damaging irradiation. Thus, the delicate intraocular structures would not be directly exposed to the effects of the laser. The invention thus provides a safe, effective and reproducible method and apparatus for modifying corneal refractive properties.

The provision of a curved ring-like deflector in preferred embodiments of the invention minimizes the need for moving parts to achieve the desired corneal refractive power correction.

Although the invention has been described in great detail above by way of reference to the accompanying drawings, it should be understood that a wide variety of embodiments may be provided within the spirit and scope of the invention and that the invention should not be limited to the specific embodiments herein disclosed, but should be interpreted only in accordance with the claims which follow.

I claim:

1. An apparatus for modifying the refractive properties of the cornea of an eye by ablating corneal tissue, comprising:
    laser means for emitting laser light;
    an annular prism positioned 360° about said cornea and having a contoured surface, said cornea having an optical zone; and
    means for directing said laser light to strike said prism, said prism being positioned to direct said light to strike the cornea tangentially about the optical zone thereof.

2. An apparatus according to claim 1, wherein said means for directing is adjustable in three dimensions in order to cooperate with said prisms to direct said laser light to a surface of the optical zone to effect said tangential striking and thereby modify corneal curvature.

3. An apparatus according to claim 2, further comprising optical means between said laser means and said directing means for forming said laser light into a ring of laser light, said ring of laser light striking the configuration of said prism through substantially 360° resulting in substantially simultaneous striking of the cornea through 360° about the optical zone.

4. An apparatus according to claim 3, wherein said optical means comprises a mask.

5. An apparatus according to claim 3, wherein said optical means includes an axicon.

6. An apparatus according to claim 3, wherein said prism is incorporated into an eye fixation device for fixing the position of the eye.

7. An apparatus according to claim 2, wherein said laser light is in the form of a beam, further comprising means for rotating said laser beam through 360° about the prism, said beam being deflected by said prism to strike the cornea about the optical zone through substantially 360°.

8. An apparatus according to claim 7, further comprising means for tracking said laser beam across said configuration in a substantially radial direction.

9. A method for in vivo modification of the refractive properties of a patient's eye, comprising the steps of:
    (a) maintaining visual fixation;
    (b) activating means for generating a ring of laser light; and
    (c) directing said ring of laser light with a ring-shaped prism, said prism being positioned 360° about the cornea of the eye and having a contoured surface, said cornea having an optical zone, causing said ring of light to be directed thereby and to strike the optical zone of the cornea tangentially through substantially 360° around the cornea.

10. A method for vitro modification of the refractive properties of a patient's eye, comprising the steps of:
    (a) activating means for generating a ring of laser light; and
    (b) directing said ring of laser light with a ring-shaped prism, said prism being positioned 360° about the cornea of the eye and having a contoured surface, said cornea having an optical zone, causing said ring of light to be directed thereby and to strike the optical zone of the cornea tangentially through substantially 360° around the cornea.

* * * * *

UNITED STATES PATENT AND TRADEMARK OFFICE
CERTIFICATE OF CORRECTION

PATENT NO. : 5,102,409
DATED : April 7, 1992
INVENTOR(S) : Barry M. Belgorod

It is certified that error appears in the above-identified patent and that said Letters Patent is hereby corrected as shown below:

On title page, item [19] "Balgorod" should read --Belgorod--.

Title page, item [76] Invenotr: "Barry M. Balgorod" should read --Barry M. Belgorod--.

In claim 10, line 1 (Col. 10, line 57) "vitro" should read --in vitro--.

Signed and Sealed this

Fourteenth Day of September, 1993

Attest:

BRUCE LEHMAN

*Attesting Officer*    *Commissioner of Patents and Trademarks*